United States Patent [19]

Hartman

[11] 4,404,966

[45] Sep. 20, 1983

[54] HEADREST FOR A CHIROPRACTIC DEVICE

[76] Inventor: Lawrence Hartman, 2015 Rowland, Royal Oak, Mich. 48067

[21] Appl. No.: 286,574

[22] Filed: Jul. 24, 1981

[51] Int. Cl.[3] .................. A61F 5/00

[52] U.S. Cl. .................. 128/69

[58] Field of Search .................. 128/69, 70, 71, 75

[56] References Cited

U.S. PATENT DOCUMENTS

| | | | |
|---|---|---|---|
| 1,582,950 | 5/1926 | Weaver et al. . | |
| 2,727,510 | 12/1955 | Thompson | 128/69 |
| 2,756,744 | 7/1956 | Thompson | 128/69 |
| 2,791,215 | 5/1957 | Thompson | 128/69 |
| 2,878,805 | 3/1959 | Sunich | 128/33 |
| 2,886,029 | 5/1959 | Thompson | 128/69 |
| 2,926,660 | 3/1960 | Thompson | 128/70 |
| 3,343,531 | 11/1967 | Thompson | 128/69 |

*Primary Examiner*—Richard J. Apley
*Assistant Examiner*—David J. Brown
*Attorney, Agent, or Firm*—Gifford, VanOphem, Sheridan & Sprinkle

[57] ABSTRACT

A headrest is provided for use with a chiropractic table and comprises a base plate and a strap for securing the base plate to the table. A support plate is hinged on one edge to one edge of the base plate so that the support plate is pivotal between an upper first position and a lower second position. A latch assembly retains the support plate in its upper first position but releases upon the application of a predetermined pressure on the support plate to permit the support plate to move to its lower second position.

5 Claims, 8 Drawing Figures

Fig-4
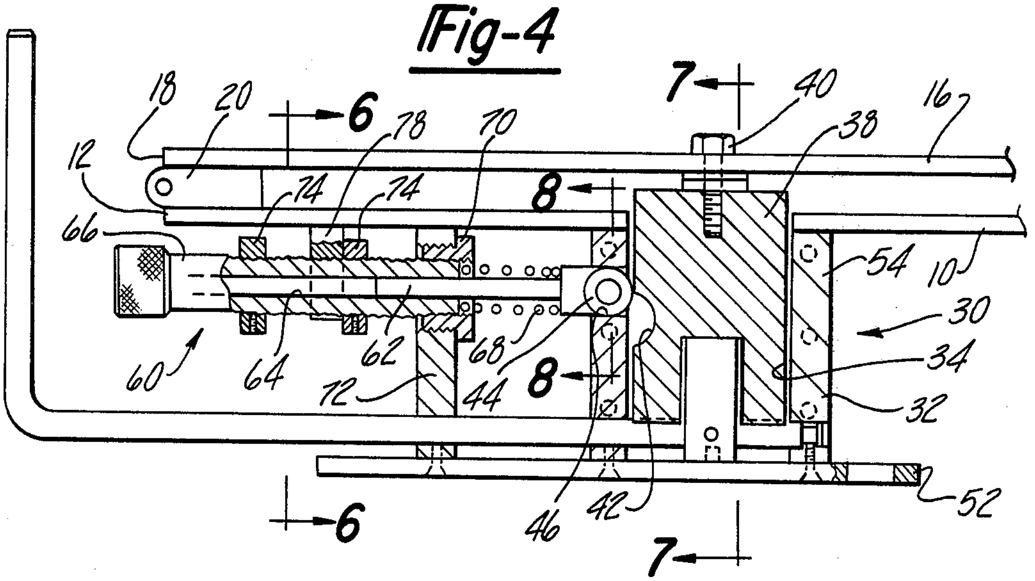
Fig-5
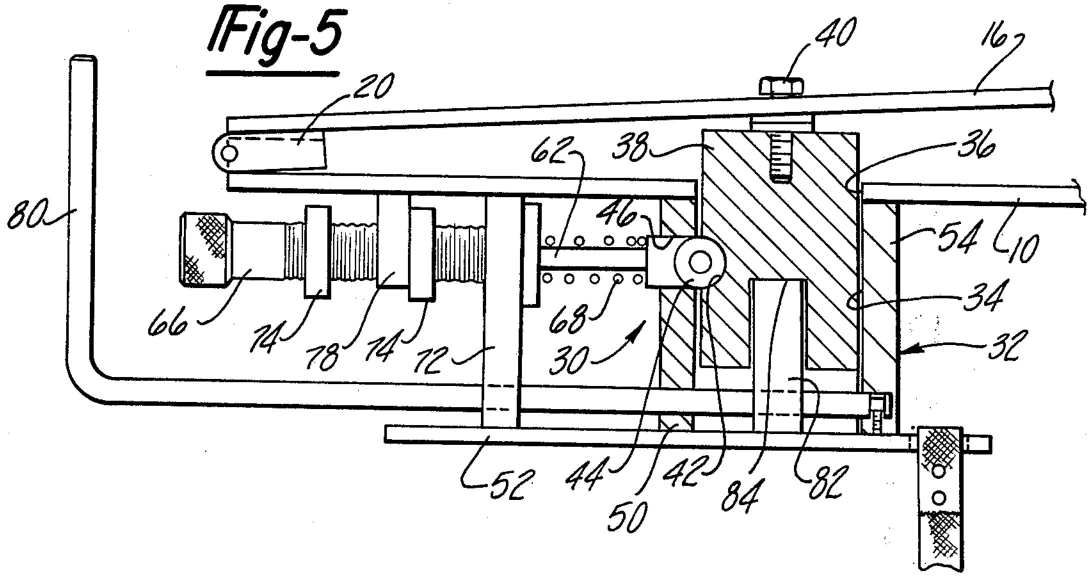
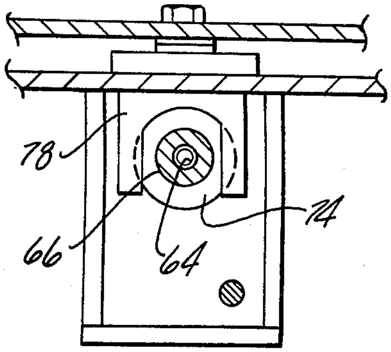
Fig-6
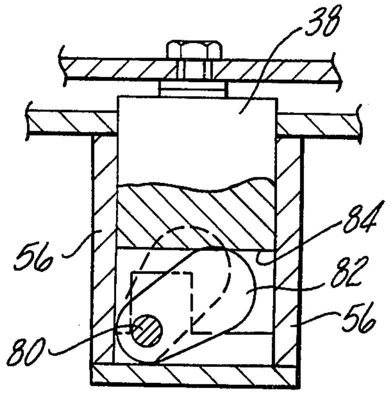
Fig-7
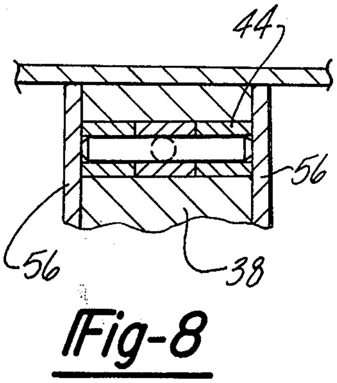
Fig-8

HEADREST FOR A CHIROPRACTIC DEVICE

BACKGROUND OF THE INVENTION

I. Field of the Invention

The present invention relates generally to chiropractic devices and, more particularly, to a headrest attachable to a chiropractic table.

II. Description of the Prior Art

It is well known that subluxations or abnormal position or condition of a vertebrae, a spinal nerve, an artery, disc or other portion of a given area in the cervical region of the human spinal column are the cause of many human ailments, such as backaches and neckaches. Furthermore, chiropractors have long been skilled in administering chiropractic adjustments for the correction of these conditions.

In order to administer chiropractic adjustments, chiropractors conventionally use an elongated cushioned table. One part of the table is used to support the body of the patient while a stationary headrest is secured or formed as a part of one end of the table. These cushioned headrests, furthermore, conventionally include a pair of longitudinally extending cushions thus forming a center crease in between. In use, the patient can then lie face down on the chiropractic table and with his or her nose positioned in the crease between the headrest cushions. The cushion then supports the head of the patient and the crease enables the patient to breath normally.

In order to administer certain types of chiropractic adjustments, and particularly chiropractic adjustments to the neck of the patient, it has been found advantageous to apply a short but sharp movement to the patient's head. Indeed, some previously known chiropractic tables include a headrest specifically designed for this type of chiropractic adjustment.

The previously known chiropractic tables having headrests designed to apply the aforementioned adjustment, however, are very expensive to obtain. Furthermore, no previously known device has been capable of converting a stationary headrest on a less expensive chiropractic table to a movable headrest of the type found on a more expensive chiropractic tables.

A still further disadvantage of the movable headrest found on some chiropractic tables is that these headrests are complex and expensive in construction. Furthermore, these movable headrests are oftentimes difficult to operate and adjust.

SUMMARY OF THE PRESENT INVENTION

The present invention provides a headrest attachable to a chiropractic table which overcomes all of the abovementioned disadvantages. In brief, the headrest according to the present invention comprises a generally rectangular base plate and means for securing the base plate to the headrest of an existing chiropractic table. Although different means can be used, in the preferred form of the invention, one or more straps are secured to the base plate which engage and fasten the base plate to the chiropractic table headrest or its frame.

The headrest of the present invention further comprises a support plate which is hinged along one edge to one edge of the base plate so that the support plate is pivotal between an upper first position, in which the support plate is spaced from the base plate, and a lower second position in which the support plate is closely adjacent the base plate. A cushion is attached to the support plate and it is upon this cushion that the patient's head is placed.

A latch assembly is attached to the base plate and normally retains the support plate in its first position. The latch assembly, however, is releasable upon the application of the predetermined pressure on the support plate in a direction towards the base plate. This predetermined pressure, however, is manually adjustable by an adjustment knob.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 4 is a sectional view taken substantially along line 4—4 in FIG. 3 and showing the headrest in a first position;

FIG. 5 is a sectional view similar to FIG. 4 but showing the headrest in a second position;

FIG. 6 is a sectional view taken substantially along line 6—6 in FIG. 4;

FIG. 7 is a fragmentary sectional view taken substantially along line 7—7 in FIG. 4; and FIG. 8 is a fragmentary sectional view taken substantially along line 8—8 in FIG. 4.

DETAILED DESCRIPTION OF A PREFERRED EMBODIMENT OF THE PRESENT INVENTION

Figure 2:
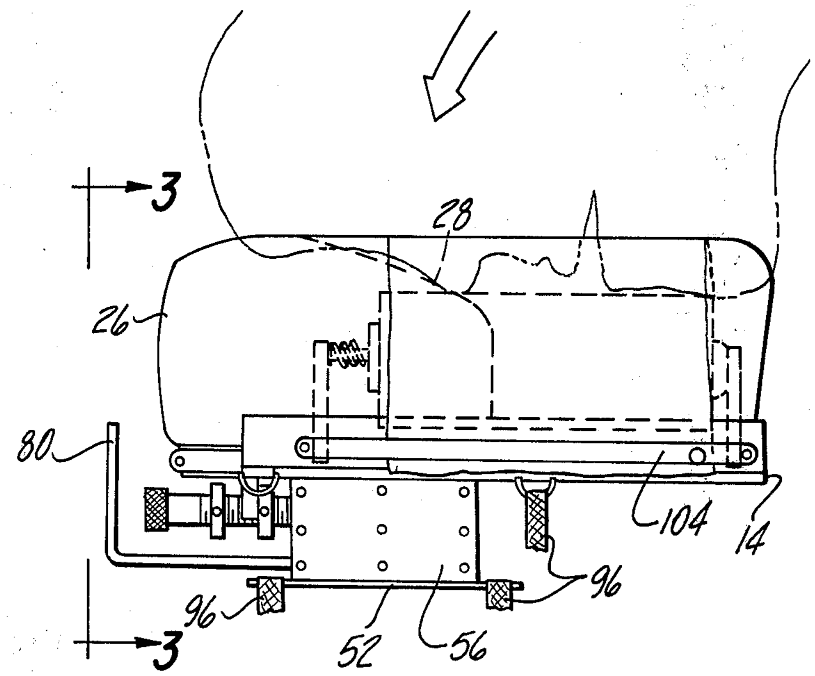
FIG. 2 is a side view of the preferred embodiment of the invention.
Figure 3:
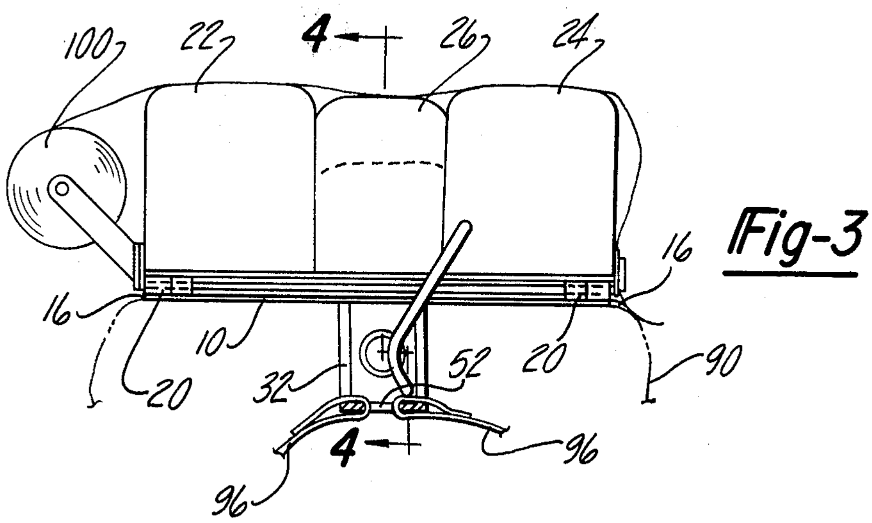
FIG. 3 is an end view taken substantially along line 3—3 in FIG. 2.

With reference first to FIGS. 2–4, a preferred embodiment of the headrest according to the present invention is thereshown and comprises a base plate 10 constructed of a rigid material, such as steel. The base plate 10 is generally rectangular in shape and thus includes a top edge 12, a bottom edge 14 (FIG. 2) and two side edges 16 (FIG. 3). A support plate 16, which is substantially the same in shape and size to the base plate 10, is pivotally mounted along its top edge 18 to the top edge 12 of the base plate 10 by hinges 20. The hinges 20 enable the support plate 16 to pivot with respect to the base plate 10 in a manner which will be subsequently described in greater detail.

Figure 1:
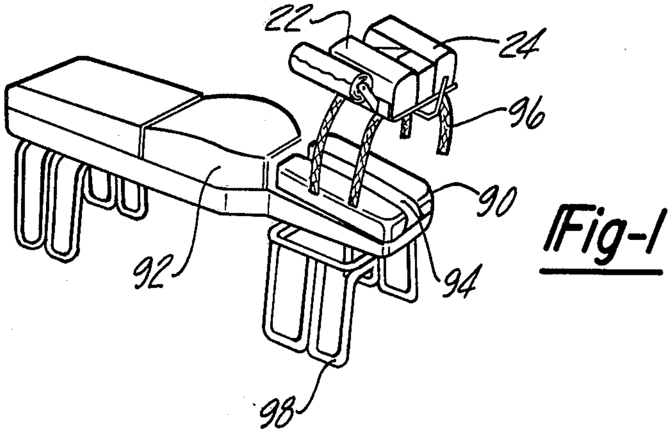
FIG. 1 is an elevational view illustrating a preferred embodiment of the headrest according to the present invention and its attachment to a chiropractic table.

With reference now to FIGS. 1–3, a pair of elongated cushions 22 and 24 are mounted along the opposite sides of the support plate 16 in any conventional fashion so that the cushions 22 and 24 are spaced apart and parallel to each other. A center cushion 26 is positioned in between the side cushions 22 and 24 and includes an angled tapered portion 28 (FIG. 2) along its center. Thus, as best shown in FIG. 2, with a patient's head positioned on and supported by the side cushions 22 and 24, the recessed portion 28 of the center cushion 26 registers with the patient's nose and enables the patient to breath freely.

With reference now to FIGS. 4 and 5, the support plate 16 is pivotal via the hinges 20 between an upper first position in which the support plate 16 is spaced apart from the base plate 10 as shown in FIG. 5, and a lower second position in which the support plate 16 is closely adjacent the base plate 10, as shown in FIG. 4.

In addition, a pressure releasable latch assembly 30 is provided between the base plate 10 and support plate 16 for maintaining the support plate 16 in its first position.

The latch assembly 30 comprises a generally rectangular channel member 32 having a front wall 50, back wall 54, side walls 56 (FIG. 7) and a lower cover 52. The channel member 32 is secured to and extends beneath the base plate 10 and defines an interior rectangular channel 34 extending in a direction substantially perpendicular to the plane of the base plate 10. This rectangular channel 34 registers with a like shaped opening 36 in the base plate 10. A rectangular plunger 38 is then secured to the support plate 16 by a bolt 40 so that the plunger 38 is slidably received within the rectangular channel 34.

Still referring to FIGS. 4, 5 and 8, a recess 42 having a semicircular cross sectional shape is formed along the side of the plunger 38 facing the front edge 12 of the base plate 10. A cylindrical detent 44 is slidably mounted through an opening 46 of the front wall 50 of the channel member 32 and registers with and nests within the recess 42 when the support plate 16 is in its first position, as shown in FIG. 5. Conversely, when the support plate 16 moves to its second position, as shown in FIG. 4, the plunger 38 forces the detent 44 out of the recess 42 and outwardly towards the front edge 12 of the base plate 10.

Referring now to FIGS. 4–6, an adjustable spring assembly 60 is provided for urging the cylindrical detent 44 toward the plunger 38 and thus towards the recess 42. The assembly 60 includes a rod 62 extending outwardly from and attached at one end to the detent 44 and which is slidably received within an elongated axial channel 64 in a cylindrical adjustment member 66. A compression spring 68 is entrapped between one end of the adjustment member 66 and the detent 44.

The adjustment member 66, furthermore, is externally threaded and threadably engages a bushing 70 (FIG. 4) mounted to a brace 72 secured between the base plate 10 and the lower cover 52. Consequently, the compression of the spring 68, and thus the force exerted on the cylindrical detent 44 towards the plunger 48, can be varied by varying the position of the adjustment member 66 with respect to its bushing 70. Collars 74 are also preferably mounted at spaced locations along the adjustment member 66 and cooperate with a stop 78 mounted to the base plate 10 to define the minimum and maximum amount of compression of the spring 68.

With reference to FIGS. 4 and 5, as thus far described and assuming that the support plate 16 is initially in its upper first position as shown in FIG. 5, the spring 68 urges the detent 44 into to cylindrical recess 42 thus holding the support plate 60 in its upper position. However, when a force greater than a predetermined amount is applied to the support plate 16 in the direction towards the base plate 10, the plunger 38 overcomes the force of the spring 68 thus forcing the detent 44 to retract to the position shown in FIG. 4 and permitting the support plate 16 to drop to its second position, also shown in FIG. 4. Furthermore, the amount of force necessary to move the support plate 16 can be adjusted by adjusting the compression of the spring 68 via the adjustment member 66.

With reference now particularly to FIGS. 5 and 7, the present invention further comprises an L-shaped handle 80 for returning the support plate 16 from its second or lower position and to its first or upper position. One leg of the handle 80 is rotatably mounted in the brace 72, front wall 50 and rear wall 54 of the channel member 32 so that the handle 80 protrudes outwardly from the front edge 12 of the base plate 10. A cam 82 is secured to the handle 80 within the rectangular recess 34 and below the plunger 38. The cam 82 cooperates with a cam follower surface 84 formed in the bottom of the plunger 38 so that pivotting of the handle 80 in a counterclockwise direction as viewed in FIG. 7 causes the cam 82 to engage the cam follower surface 84 and move the plunger 38 with its attached support plate 16 to its upper first position. If desired, a roller (not shown) can be attached to the cam 82 to engage the cam follower surface 84 thus reducing frictional wear and tear between the cam 82 and cam follower surface 84.

With reference now to FIGS. 1 and 3, the entire headrest is adapted to be secured to a stationary headrest 90 on a chiropractic table 92. In attaching the headrest to the stationary headrest 90, the channel member 32 which extends downwardly from the base plate 10 nests in between the center groove 92 conventionally found on the stationary headrest 90 of chiropractic tables 92. Consequently, the headrest according to the present invention extends above the conventional stationary headrest 90 only slightly more than the thickness of the cushions 22, 24 and 27. Furthermore, the headrest is secured to the stationary headrest 90 through one or more straps 96 secured to the base plate 10 and/or the lower cover 52 on the channel member 32. The straps 96 extend around at least a portion of the frame 98 of the chiropractic table 92 and have their free ends secured together in any conventional fashion.

Still referring to FIGS. 1 and 3, in the preferred form of the invention a paper roll 100 is mounted to the outside of the cushion 22 and dispenses paper over and across the cushions 22, 24 and 26. The opposite end of the paper is secured in place by an elongated lever 104 (FIG. 2) pivotally mounted to the base plate on the outside of the other cushion 24. The paper roll 100 is provided purely for sanitary reasons.

With reference now to FIG. 2, in operation the upper support plate 16 with its attached cushions 22–26 is first moved to its upper or first position by the handle 80 in the previously described fashion and the patient's head is then positioned on the cushions. The chiropractor then applies a downward pressure on the patient's head toward the cushion, and, when this pressure exceeds the predetermined amount as determined by the setting of the adjustment members 66 and compression of the spring 68, the support plate 16 with its attached cushions snaps to its lower or second position thus providing the desired chiropractic adjustment. This procedure can be repeated as required.

It can thus be seen that the headrest according to the present invention is advantageous in several different respects. First, the headrest is advantageous in that it can be secured to the stationary headrest 90 of a conventional chiropractic table 92 thus obtaining the advantages of the chiropractic table 92 with a movable headrest but at a fraction of the cost.

A still further advantage of the present invention is that both the handle 80 for returning the support plate to the upper position as well as the adjustment member 66 extend through the groove 94 between the cusions of the stationary headrest 90 and are accessible outwardly from the front edge of the headrest. This location for both the handle 80 and adjustment member 66 facilitates the use of the headrest of the chiropractor.

A still further advantage of the headrest according to the present invention is that it is relatively simple and, therefore, inexpensive in construction. Furthermore, although inexpensive in construction, the headrest of the present invention is totally effective in use.

A still further advantage of the headrest according to the present invention is that the headrest is portable can can be moved from one table and to another.

A yet further advantage of the headrest of the present invention is that the lever for moving the support plate from its lower and to its upper position nests in between and extends outwardly from the head cushions on a conventional chiropractic table. This provision enables the portable headrest of the present invention to maintain a low profile when attached to the table.

Having described my invention, however, still further modifications thereto will become apparent to those skilled in the art to which it pertains without deviation from the spirit of the invention as defined by the scope of the appended claims.

I claim:

1. A portable headrest for use with a chiropractic table of the type having a pair of stationary headrests spaced apart from each other and forming a space therebetween, said portable headrest comprising:

a base plate having an upper end and a lower surface, means for securing said base plate to said stationary headrests, a support plate, means pivotally securing one edge of said support plate to one edge of said base plate so that said support plate is pivotal between a first position in which said support plate is spaced outwardly from said upper surface of said base plate, and a second position in which said support plate is positioned closely adjacent said base plate, a channel member secured to a midpoint of said base plate, said channel member extending outwardly from said lower surface of said base plate and said channel member being dimensioned to fit in said space between said stationary headrests, latch means for retaining said support plate in said first position, said latch means being at least partly contained within said channel member and releasable upon application of a predetermined pressure on said support plate in a direction towards said base plate, means for moving said support plate from said second position and to said first position, said moving means comprising an elongated handle extending outwardly from one end of said channel member so that said handle extends through said space between said stationary headrests, said handle having a free end extending outwardly from said one edge of said base plate, and means for variably adjusting the release pressure of said latch means, said adjusting means comprising an adjustment member extending outwardly from said one end of said channel member extends through said space between said stationary headrests, said adjustment member having a free end positioned adjacent said one edge of said base plate.

2. The invention as defined in claim 1 wherein said securing means comprises at least one strap secured at one end to each side of the base plate and means for securing the free ends of the straps together.

3. The invention as defined in claim 1 wherein said latch means comprises:

a plunger attached at one end to said support plate, said plunger having a recess formed on one side, said plunger being slidably received in said channel member, a detent slidably mounted to said base plate, said detent extending through an opening in said channel member and registering with said recess when said support plate is in said first position, and means for resiliently urging said detent towards said plunger.

4. The invention as defined in claim 3 wherein said resilient means comprises a compression spring and wherein said adjusting means comprises means for varying the compression of said spring.

5. The invention as defined in claim 3 wherein said moving means comprises:

a cam rotatably mounted within said channel member adjacent the other end of the plunger, and said handle being secured to said cam.

* * * * *

UNITED STATES PATENT AND TRADEMARK OFFICE

CERTIFICATE OF CORRECTION

PATENT NO. : 4,404,966

DATED : September 20, 1983

INVENTOR(S) : Lawrence Hartman

It is certified that error appears in the above—identified patent and that said Letters Patent is hereby corrected as shown below:

Column 1, line 44 delete "tables" insert --table--.

Column 3, line 52 delete "to".

Column 5, line 7 delete "can" first occurrence, insert --and--.

Signed and Sealed this

*Third* Day of *July 1984*

[SEAL]

*Attest:*

GERALD J. MOSSINGHOFF

*Attesting Officer* *Commissioner of Patents and Trademarks*